United States Patent [19]
Thompson et al.

[11] Patent Number: 5,342,334
[45] Date of Patent: Aug. 30, 1994

[54] COEXTRUDED THREE-DIMENSIONAL FLUID-PERVIOUS PLASTIC WEB

[75] Inventors: Hugh A. Thompson, Fairfield; Fred M. Langdon, Cincinnati, both of Ohio

[73] Assignee: The Procter & Gamble Company, Cincinnati, Ohio

[21] Appl. No.: 42,345

[22] Filed: Apr. 2, 1993

[51] Int. Cl.⁵ .................. A61F 13/15; A61F 13/20
[52] U.S. Cl. .................. 604/366; 604/358; 604/367; 604/370; 604/378; 604/385.1
[58] Field of Search ............. 604/358, 365, 366, 367, 604/370, 378, 384, 385.1

[56] References Cited
U.S. PATENT DOCUMENTS

| | | | |
|---|---|---|---|
| 4,315,507 | 2/1982 | Whitehead et al. | 604/366 |
| 4,342,314 | 8/1982 | Radel et al. | |
| 4,681,577 | 7/1987 | Stern et al. | 604/370 |
| 4,690,679 | 9/1987 | Mattingly, III et al. | |
| 4,710,186 | 12/1987 | DeRossett et al. | |
| 4,806,411 | 2/1989 | Mattingly, III et al. | |
| 4,883,707 | 11/1989 | Newkirk | 604/370 |
| 5,006,394 | 4/1991 | Baird | |
| 5,069,677 | 12/1991 | Sakurai et al. | 604/370 |
| 5,078,710 | 1/1992 | Suda et al. | 604/366 |
| 5,135,521 | 8/1992 | Luceri et al. | 604/370 |
| 5,143,779 | 9/1992 | Newkirk et al. | 604/378 |

*Primary Examiner*—Randall L. Green
*Assistant Examiner*—P. Zuttarelli
*Attorney, Agent, or Firm*—Kevin C. Johnson; E. Kelly Linman

[57] ABSTRACT

The present invention provides an absorbent article including a fluid pervious topsheet, a fluid impervious backsheet joined to the topsheet, and an intermediate layer positioned between the topsheet and the backsheet. The topsheet comprises: a resilient, three-dimensional, macroscopically expanded, fluid pervious web including a first polymeric material which exhibits a first melting point temperature and a second polymeric material bonded to the first polymeric material to form a laminate. The second polymeric material exhibits a second melting point temperature which is less than the first melting point temperature. The web has first and second surfaces spaced apart by a distance greater than the thickness of the laminate. The web includes a plurality of capillaries extending from the first surface to the second surface. The capillaries are defined by a plurality of sidewall portions interconnected to one another intermediate the first and the second surfaces and terminating in the second surface, such that when the web is heated to a temperature between the first melting point temperature and the second melting point temperature the second polymeric material of the sidewall thermally bonds to the intermediate layer along the second surface of the web.

22 Claims, 7 Drawing Sheets

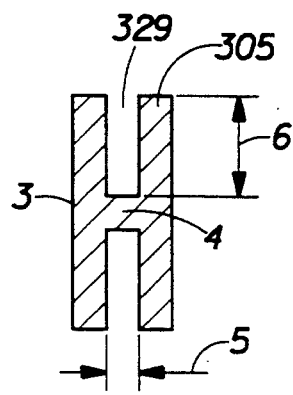
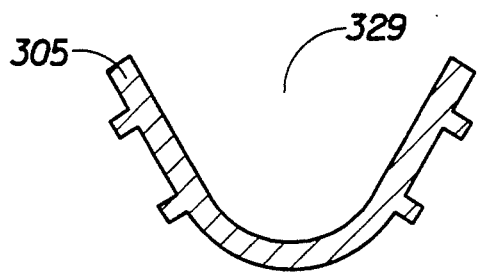
Fig. 8           Fig. 9
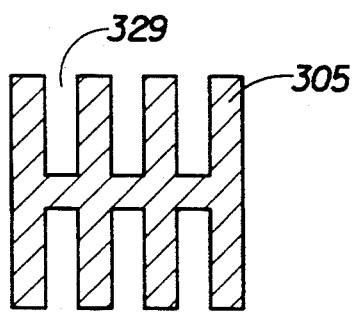
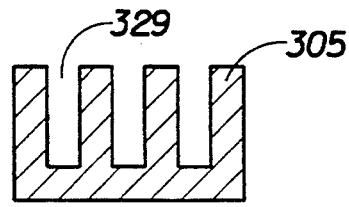
Fig. 10          Fig. 11
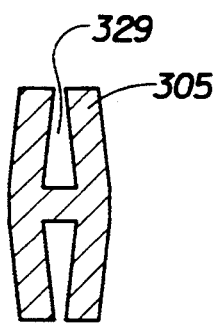 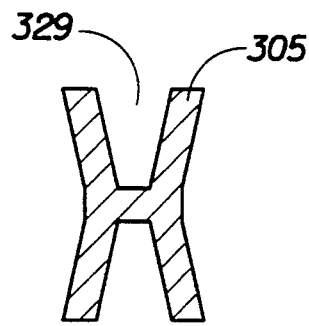 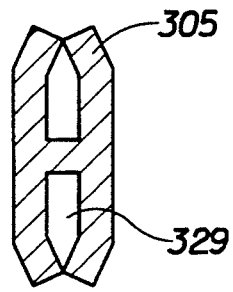
Fig. 12A          Fig. 12B          Fig. 12c

COEXTRUDED THREE-DIMENSIONAL FLUID-PERVIOUS PLASTIC WEB

TECHNICAL FIELD

The present invention relates to resilient, three-dimensional fluid-pervious, plastic webs for use as topsheets on absorbent articles, especially catamenial articles, and more particularly, to such webs including a first polymeric material and a second polymeric material secured together to form a laminate. The first polymeric material exhibits a melting point temperature greater than the melting point temperature of the second polymeric material such that when the three-dimensional web is heated to a temperature between the first melting point temperature and the second melting point temperature the second polymeric material is thermally bonded to the underlying layer of the absorbent article, e.g., the absorbent core.

BACKGROUND OF THE INVENTION

It has long been known in the disposable absorbent bandage art that it is extremely desirable to construct absorptive devises such as disposable diapers, catamenials, sanitary napkins, incontinent articles, and the like, presenting a dry surface feel to the user to improve wearing comfort and to minimize the development of undesirable skin conditions due to prolonged exposure to moisture absorbed within the bandage.

One viable prior art solution to the aforementioned problem is disclosed in commonly assigned U.S. Pat. No. 4,342,314 issued to Radel and Thompson on Aug. 3, 1982 and hereby incorporated herein by reference. Radel et al. discloses an absorbent bandage with a wearer-contacting topsheet comprising a resilient macroscopically expanded, three-dimensional, plastic web exhibiting a combination of fiber-like and plastic properties. In a preferred embodiment, the macroscopically expanded, three-dimensional, plastic web topsheet disclosed in Radel et al. exhibits a fine scale three-dimensional microstructure comprising capillary networks originating in and extending from one surface of the web and terminating in the form of apertures in the opposite surface thereof to promote rapid fluid transport. The web's fiber-like appearance is comprised of a continuum of fiber-like elements, the opposed ends of each of the fiber-like elements are interconnected to at least one other of the fiber-like elements.

A typical capillary network in the Radel et al. structure comprises an uppermost capillary opening formed by a multiplicity of primary fiber-elements interconnected to one another in the uppermost plane of the web. The uppermost opening may, if desired, be further subdivided into smaller capillary openings by secondary and tertiary fiber-like elements at planes located below the wearer-contacting surface of the web.

Each of the fiber-like elements exhibits a substantially uniform U-shaped cross-section along its length. In the case of a primary fiber-like element, its cross-section comprises a base portion located in the wearer-contacting plane and a sidewall portion joined to each edge of the base portion, the sidewall portions extend generally in the direction of the absorbent pad-contacting surface of the web. The sidewall portions which intersect one another are joined to one another intermediate the wearer contacting surface and the absorbent pad contacting surface of the web, thereby forming a capillary network interconnecting the opposed surfaces of the web. The secondary and tertiary fiber-like elements, when employed, are generally similar, but originate in planes below the wearer-contacting surface of the web.

A topsheet of the type generally disclosed by Radel et al. is highly effective in promoting rapid fluid transfer from the first wearer-contacting surface to the second absorbent pad-contacting surface of the topsheet. Accordingly, topsheets of this type have enjoyed widespread commercial success on catamenial pads due to their clean and dry appearance in use when contrasted to conventional nonwoven fibrous topsheets. While the Radel et al. topsheet is highly effective in promoting rapid transfer of bodily fluids from the first wearer-contacting surface to the second absorbent pad-contacting surface, the topsheet is secured to the absorbent core with an adhesive. Unfortunately, adhesives have a tendency to clog the apertures if applied too heavily. If the apertures become clogged, fluid is not permitted to drain through the topsheet thereby exposing the skin to moisture. In addition, bonding layers together with an adhesive to ensure fluid transporting contact throughout can produce a stiff structure which is uncomfortable. Furthermore, adhesives may not provide sufficient contact between the topsheet and the underlying layers if applied too sparingly or may be rendered useless when wetted with body exudate.

Another prior art attempt at securing a topsheet to the underlying layer is disclosed in U.S. Pat. Nos. 4,690,679 issued Sep. 1, 1989 and U.S. Pat. No. 4,806,411 issued Feb. 21, 1989 to Mattingly, III et al. Both of these patents disclose a coextruded, apertured, two-dimensional film suitable for use as topsheet on a sanitary napkin. The coextruded film comprises a first layer of a first polymeric material and a second layer of a second polymeric material. Both layers are apertured for the transmission of bodily fluids therethrough. The first polymeric material exhibits a melting point temperature which is greater than the melting point temperature exhibited by the second polymeric material. The apertured film may be thermally bonded by heating the film to a temperature in excess of the melting point temperature of the second layer material and below the melting temperature of the first layer material. While this two-dimensional apertured film may be well suited for thermal bonding it would not function well as a topsheet on an absorbent article. Since the entire nonaperatured portion of the second polymeric material will be thermally bonded to the underlying layer, e.g., the absorbent core, a relatively stiff sanitary napkin will be created due to the excessive amount of bonding between the topsheet and the absorbent core. Furthermore, the two-dimensional topsheet does not provide sufficient standoff from the absorbent core for the wearer. Accordingly, even as fluid is permitted to pass through the apertures provided in the two-dimensional topsheet, the wearer's skin is placed in intimate contact with the bodily fluids which have been absorbed by the absorbent core.

Accordingly, it is desirable to provide an absorbent article having a topsheet sheet which may be thermally bonded to the absorbent core and yet maintain the flexibility, resilience, and standoff of the prior art commercially successful three-dimensional formed-film topsheets.

SUMMARY OF THE INVENTION

The present invention pertains, in a preferred embodiment, to an absorbent article including a fluid pervious topsheet, a fluid impervious backsheet joined to the topsheet, and an intermediate layer positioned between the topsheet and the backsheet. The topsheet comprises, a resilient, three-dimensional, macroscopically expanded, fluid pervious web including a first polymeric material which exhibits a first melting point temperature and a second polymeric material bonded to the first polymeric material to form a laminate. The second polymeric material exhibits a melting point temperature which is less than the first melting point temperature. The web has first and second surfaces spaced apart by a distance greater than the thickness of the laminate. The web has a plurality of capillaries extending from the first surface to the second surface. The capillaries are defined by a plurality of sidewall portions interconnected to one another intermediate the first and second surfaces and terminate in the second surface, such that when the web is heated to a temperature between the first melting point temperature and the second melting point temperature the second polymeric material of the sidewall thermally bonds to the intermediate layer.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify identical elements and wherein:

FIG. 8 is a cross-sectional view of a symmetrical "H"-shaped capillary channel fiber with a planar base (4), with between walls (5), and a depth-of-walls (6);

FIG. 9 is a cross-sectional view of a "C"-shaped capillary channel fiber having stabilizing legs;

FIG. 10 is a cross-sectional view of a multiple "H"-shaped capillary channel fiber;

FIG. 11 is a cross-sectional view of a multiple "U"-shaped capillary channel fiber;

FIG. 12A is a cross-sectional view of an "H"-shaped capillary channel fiber and a partially collapsed state;

FIG. 12B is a cross-sectional view of an expanded capillary channel fiber;

FIG. 12C is a cross-sectional view of a wholly collapsed capillary channel fiber.

DETAILED DESCRIPTION OF THE INVENTION

1. General Description of the Absorbent Article

As used herein, the term "absorbent article" refers to devices which absorb and contain body exudates, and, more specifically, refers to devices which are placed against or in proximity to the body of the wearer to absorb and contain the various exudates discharged from the body. The term "absorbent article" is intended to include diapers, catamenial pads, sanitary napkins, pantiliners, incontinent pads, and the like. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
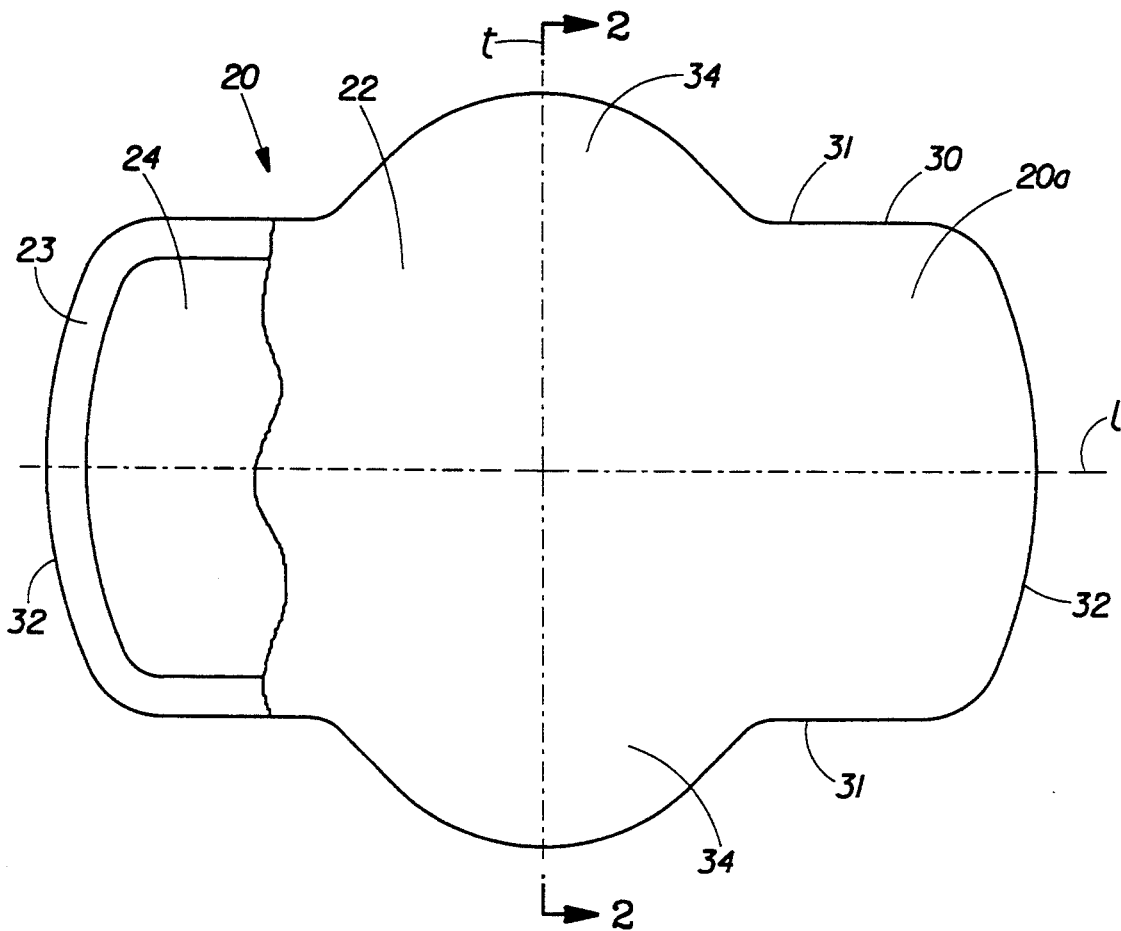
FIG. 1 is a top plan view of a sanitary napkin with portions cut-away to more clearly show the construction of the sanitary napkin.

A preferred embodiment of a unitary disposable absorbent article is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

The sanitary napkin 20 has two surfaces, a wearer-contacting surface or body-contacting surface or "body surface" 20a and a garment surface 20b. The sanitary napkin 20 is shown in FIG. 1 as viewed from its body surface 20a. The body surface 20a is intended to be worn adjacent to the body of the wearer. The garment surface 20b of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline "l" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

FIG. 1 is a top plan view of the sanitary napkin 20 of the present invention in its flat-out state with portions of the structure being cut-away to more clearly show the construction of the sanitary napkin 20 and with the portion of the sanitary napkin 20 which faces or contacts the wearer 20a, oriented towards the viewer. As shown in FIG. 1, the sanitary napkin 20 preferably comprises a liquid pervious topsheet 22, a liquid impervious backsheet 23 joined with the topsheet 22, and an absorbent core 24 positioned between the topsheet 22 and the backsheet 23.

FIG. 1 also shows that the sanitary napkin 20 has a periphery 30 which is defined by the outer edges of the sanitary napkin 20 in which the longitudinal edges (or "side edges") are designated 31 and the end edges (or "ends") are designated 32.

Sanitary napkin 20 preferably includes optional side flaps or "wings" 34 that are folded around the crotch portion of the wearer's panties. The side flaps 34 can serve a number of purposes, including, but not limited to protecting the wearer's panties from soiling and keeping the sanitary napkin secured to the wearer's panties.

Figure 2:
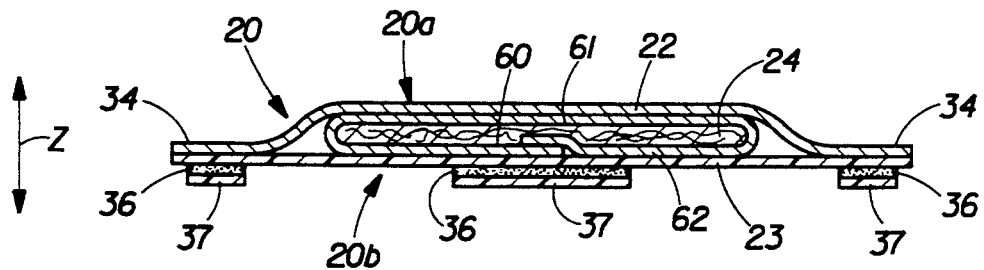
FIG. 2 is a cross-sectional view of the sanitary napkin of FIG. 1 taken along line 2—2.

FIG. 2 is a cross-sectional view of the sanitary napkin 20 taken along section line 2—2 of FIG. 1. As can be seen in FIG. 2, the sanitary napkin 20 preferably includes an adhesive fastening means 36 for attaching the sanitary napkin 20 to the undergarment of the wearer. Removable release liners 37 cover the adhesive fastening means 36 to keep the adhesive from sticking to a surface other than the crotch portion of the undergarment prior to use.

In addition to having a longitudinal direction and a transverse direction, the sanitary napkin 20 also has a "z" direction or axis, which is the direction proceeding down through the topsheet 22 and into whatever fluid storage core 24 that may be provided. The objective is to provide a continuous path between the topsheet 22 and underlying layer or layers of the articles herein, such that fluid is eventually drawn in the "z" direction and away from the topsheet of the article into its ultimate storage layer. In a preferred embodiment the continuous path will have a gradient of increasing capillary attraction which facilitates fluid flow down into the storage medium.

The individual components of the sanitary napkin will now be looked at in greater detail.

2. Individual Components of the Sanitary Napkin

A. The Topsheet

Figure 3:
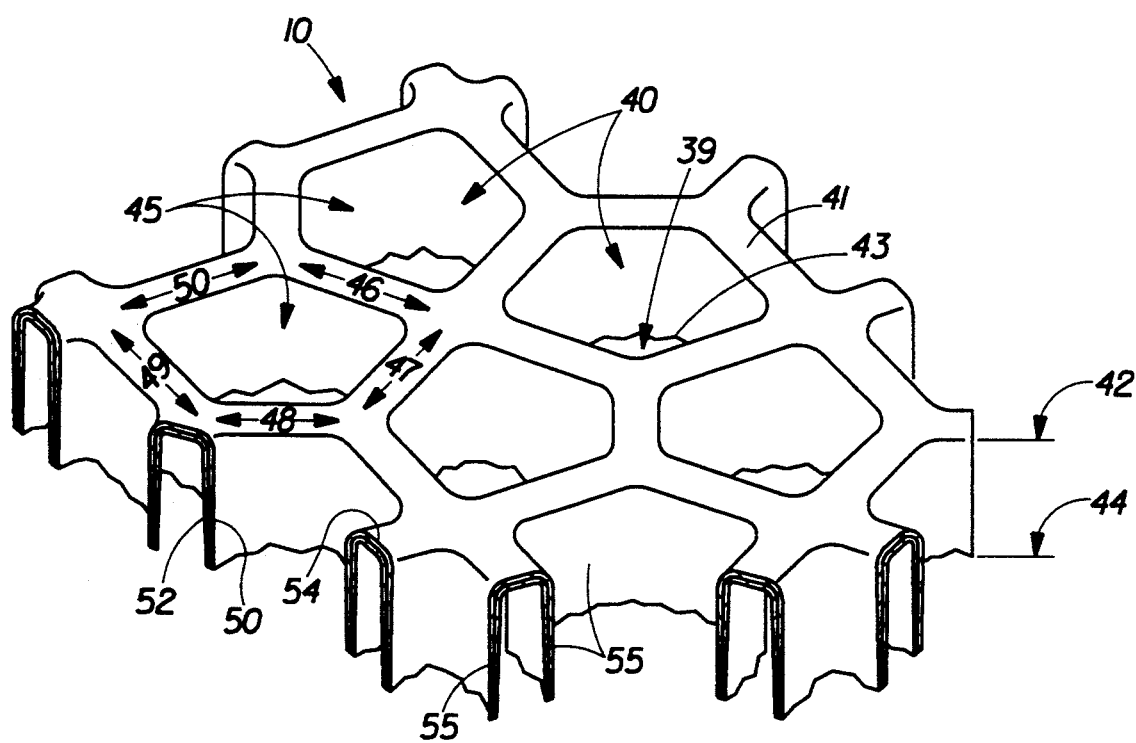
FIG. 3 is an enlarged, partially segmented, perspective illustration of a preferred resilient, three-dimensional, macroscopically expanded, fluid pervious, web of the present invention.

FIG. 3 is an enlarged partially segmented, perspective illustration of a preferred embodiment of a resilient, three-dimensional, macroscopically expanded, fluid pervious, plastic web 10 which has been found suitable for use as a topsheet on disposable absorbent articles, such as the sanitary napkin 20 illustrated in FIGS. 1 and 2. As utilized herein, the term "macroscopically expanded", when used to describe three-dimensional plastic webs, ribbons and films, refers to webs, ribbons and films which have been caused to conform to the surface of a three-dimensional forming structure so that both surfaces thereof exhibit the three-dimensional pattern of said forming structure, said pattern being readily visible to the naked eye when the perpendicular distance between the viewer's eye and the plane of the web is about 12 inches. As can be seen in FIG. 3, the web 10 is comprised of a first polymeric material 50 and a second polymeric material 52 secured to the first polymeric material to form a laminate. Preferably the laminate web 10 is formed by the coextrusion of two polymers.

The first polymeric material 50 exhibits a first melting point temperature. The second polymeric material 52 exhibits a second melting point temperature which is less than the melting point temperature of the first material 50. As used herein, the term "melting point" refers to the temperature at the peak of the melting endotherm, at which point the solid and liquid states are in equilibrium.

Preferably, the web 10 is comprised of a continuum of fiber-like elements, the opposed ends of each of the fiber-like elements are interconnected to at least one another of the fiber-like elements to give the web 10 a fiber-like appearance. In the embodiment disclosed in FIG. 3, the interconnected fiber-like elements form a pattern of pentagonally shaped capillaries 40. The web 10, which exhibits a fiber-like appearance, embodies a three-dimensional structure comprising capillaries 40 extending from the web's uppermost or wearer-contacting surface 41 in plane 42 to its lowermost or absorbent pad contacting surface 43 in plane 44 to promote rapid fluid transport from the uppermost surface 41 to the lowermost surface 43 of the web 10 without lateral transmission of fluid between adjacent capillaries 40.

Apertures 45 are formed by a multiplicity of intersecting fiber-like elements, e.g., elements 46, 47, 48, 49, and 50, interconnected to one another in the first surface of the web. Each fiber-like element comprises a base portion, e.g., base portion 54, located in plane 42. Each base portion has a sidewall portion, e.g., sidewall portions 55, attached to each edge thereof. The sidewall portions 55 extend generally in the direction of the second surface 43 of the web. The intersecting sidewall portions of the fiber-like elements are interconnected to one another intermediate the first and second surfaces of the web and terminate substantially concurrently with one another in the plane 44 of the second surface.

In a particularly preferred embodiment, the interconnected sidewall portions terminate substantially concurrently with one another in the plane of the second surface 44 to form apertures 39 in the second surface 43 of the web. The capillaries 40 formed by the interconnected sidewall portions allow for free transfer of fluids from the first surface 41 of the web directly to the second surface 43 Of the web without lateral transmission of the fluid between adjacent capillary networks.

Preferably, the web 10 is formed by the coextrusion of two polymers. The polymers used for top layer 50 and bottom layer 52 should both be flexible. In addition, the two polymers chosen should have adequate strength to withstand the normal wear and tear expected when used as a topsheet on an absorbent article.

The main criterion for selecting the polymers to be used for the uppermost layer 50 and the lowermost layer 52 is the melting point temperature differential between any two possible polymers. Once a polymer for one layer is selected, the polymer for the other layer can be chosen such that the polymer of the uppermost layer 50 has a higher melting point temperature than that of the lowermost layer 52. The melting point temperature of the lowermost layer 52 should be matched with the thermal bonding component of the intermediate layer of the sanitary napkin.

Suitable polymers for the uppermost layer 50 include low density polyethylene (LDPE), medium density polyethylene (MDPE), high density polyethylene (HDPE), linear low density polyethylene (LLDPE), polypropylene and blends thereof. Suitable polymers or materials for the lowermost layer 52 include polymers bondable to the materials used for uppermost layer 50 above, but of lower melting point temperature, ethylene vinyl acetate (EVA) and blends thereof. In a particularly preferred embodiment, the uppermost layer 50 comprises a LDPE/LLDPE blend and the lowermost layer 52 comprises a blend of LDPE/EVA.

In another embodiment, the melting point temperature of the uppermost layer is less than the melting point temperature of the lowermost layer. As with the previous embodiment, the main criterion for selecting the polymers to be used for the uppermost and lowermost layers is the melting point temperature differential between any two possible polymers. Once a polymer for one layer is selected, the polymer for the other layer can be chosen such that the polymer of the uppermost layer has a lower melting point temperature than that of the lowermost layer.

B. The Absorbent Core

The absorbent core 24 may be any absorbent means which is capable of absorbing or retaining liquids (e.g., menses and/or urine). As shown in FIGS. 1 and 2, the absorbent core 24 has a body surface, a garment surface, side edges, and end edges. The absorbent core 24 may be manufactured in wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. An example of other suitable absorbent materials include creped cellulose wadding; meltblown polymers including coform; chemically stiffened, modified or cross-linked cellulosic fibers; capillary channel fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core 24 may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core 24 should, however, be compatible with the design loading and the intended use of the sanitary napkin 20. Further, the size and absorbent capacity of the absorbent core 24 may be varied to accommodate different uses such as incontinence pads, pantiliners, regular sanitary napkins, or overnight sanitary napkins.

Exemplary absorbent structures for use as the absorbent core 24 of the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; U.S. Pat. No. 5,009,653 issued to Osborne on Apr. 23, 1991; and European Patent Application No. 0 198 683, The Procter & Gamble Company, published Oct. 22, 1986 in the name of Duenk et al. Each of these patents are incorporated herein by reference.

A preferred embodiment of the absorbent core 24 comprises the laminate structure shown in FIG. 2. The laminate is comprised of a layer of superabsorbent polymeric (or absorbent gelling material) and one or more sheets or webs of cross-linked cellulosic fibers. Suitable cross-linked cellulosic fibers for the absorbent core 24 are described in U.S. Pat. No. 4,888,093 issued to Cook et al. on Dec. 19, 1989; U.S. Pat. No. 4,822,543 issued to Dean et al. on Apr. 18, 1989; U.S. Pat. No. 4,889,595 issued to Schoggen et al. on Dec. 26, 1989; and U.S. Pat. No. 4,898,642 issued to Moore et al. on Feb. 6, 1990; U.S. Pat. No. 4,935,022 issued Jun. 19, 1990 to Lash et al.; EPO Patent Application Publication Nos. 0 427 316 A2 and 0 427 317 A2 published in the name of Herron et al. on May 15, 1991; and EPO Patent Application Publication No. 0 429 112 A2 published in the name of Herron et al. on May 29, 1991 incorporated herein by reference.

The cross-linked cellulosic fibers in the embodiment shown in FIG. 2 comprises a single sheet that wraps the layers of particles of absorbent gelling material 60. The sheet is wrapped so that it appears as having a "c" configuration when viewed from the end. The wrapped sheet forms an upper layer 61 and a lower layer 62. In alternative embodiments, the laminate can be formed in many other manners, such as by providing separate webs of cross-linked cellulosic material (or other absorbent material) for the different layers of the absorbent core laminate other than a single sheet, or by providing it with additional layers.

In this type of core, curled, twisted, preferably chemically stiffened and cross-linked, cellulose fibers are refined to provide fibers which can be used in sheet form as the absorbent core. The preparation of suitable curled, chemically stiffened cellulosic fibers from which one can prepare the refined, curled, chemically stiffened cellulosic fibers used in detail in U.S. Pat. Nos. 4,888,903; 4,822,543; 4,889,595; 4,889,597; 4,889,596; and 4,898,642.

The use of such fibers in combination with absorbent gelling materials, and means for manufacturing such combinations, are described in U.S. Pat. No. 4,935,022. Such preparations typically involve the use of aldehydes, such as glutaraldehyde, as crosslinking agents. In addition, polycarboxylic acids can be used as crosslinking agents. It will be appreciated that other means for preparing other crosslinked cellulosic fibers are also known, and such fibers may also be used herein, although the fluid absorbency properties may be suboptimal as compared with the above-mentioned fibers. Reference can be made to the various citations in U.S. Pat. No. 4,898,642 and PCT U.S. 89 01581 for other fiber types. Once in hand, the curled cellulosic fibers are refined to provide the fibers used to prepare the preferred absorbent cores used in the practice of this invention.

C. Backsheet

The backsheet 23 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 23 prevents the exudates absorbed and contained in the absorbent core 24 from wetting articles which contact the sanitary napkin 20 such as pants, pajamas and undergarments. The backsheet 23 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet 23 is preferably embossed and/or matte finished to provide a more clothlike appearance. Further, the backsheet 23 may permit vapors to escape from the absorbent core 24 (i.e., breathable) while still preventing exudates from passing through the backsheet 23.

D. Optional Retaining Means

In use, the sanitary napkin 20 can be held in place by any support means or attachment means well-known for such purposes. Preferably, the sanitary napkin is placed in the user's undergarment or panty and secured thereto by a fastener such as an adhesive 36. The adhesive 36 provides a means for securing the sanitary napkin 20 in the crotch portion of the panty. Thus, a portion or all of the outer surface of the backsheet 23 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the national Starch and Chemical Company of Bridgewater, N.J. Suitable adhesive fasteners are also described in U.S. Pat. No. 4,917,697. Before the sanitary napkin is placed in use, the pressure-sensitive adhesive 36 is typically covered with a removable release liner 37 in order to keep the adhesive 36 from drying out or adhering to a surface other than the crotch portion of the panty prior to use. Suitable release liners 37 are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/0 both of which are manufactured by the Akrosil Corporation of Menasha, Wis. The sanitary napkin 20 of the present invention is used by removing the release liner 37 and thereafter placing the sanitary napkin 20 in a panty so that the adhesive 36 contacts the panty. The adhesive 36 maintains the sanitary napkin in its position within the panty during use.

E. Optional Features

The sanitary napkin 20 may also be provided with two flaps 34, each of which are adjacent to and extend laterally from the side edge of the absorbent core. The flaps 34 are configured to drape over the edges of the wearer's panties in the crotch region so that the flaps 34 are disposed between the edges of the wearer's panties and the thighs.

The flaps 34 serve as least two purposes. First, the flaps 34 help serve to prevent soiling of the wearer's body and panties by menstral fluid, preferably by forming a double wall barrier along the edges of the panties. Second, the flaps 34 are preferably provided with attachment means on their garments surface so that the flaps 34 can be folded back under the panty and attached to garment facing side of the panty. In this way, the flaps 34 serve to keep the sanitary napkin 20 properly positioned in the panty.

The flaps 34 can be constructed of various materials including materials similar to the topsheet, backsheet, tissue, or combinations of these materials. Further, the flaps 34 may be a separate element attached to the main body portion of the napkin or can comprise extensions of the topsheet 22 and the backsheet 23 (i.e., unitary).

A number of sanitary napkins having flaps suitable or adaptable for use with the sanitary napkins of the present invention are disclosed in U.S. Pat. No. 4,687,478 entitled "Shaped Sanitary Napkin with Flaps", issued to Van Tilburg on Aug. 18, 1987; U.S. Pat. No. 4,589,876 entitled "Sanitary Napkin", issued to Van Tilburg on May 20, 1986; and U.S. Pat. No. 4,608,047, entitled "Sanitary Napkin Attachment Means", issued to Medingly on Aug. 26, 1986.

F. Optional Layers

Figure 6:
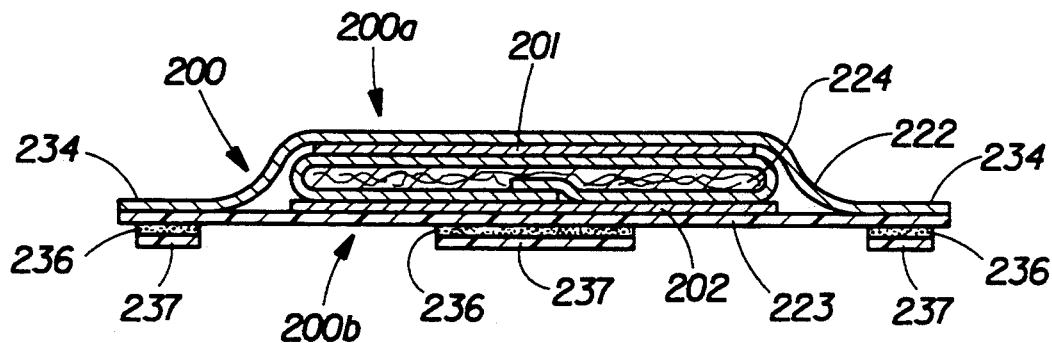
FIG. 6 is a cross-sectional view of another embodiment of a sanitary napkin of the present invention.

Referring now to FIG. 6, another embodiment of a sanitary napkin 200 is illustrated. The sanitary napkin 200 has a body surface 200a and a garment surface 200b. The sanitary napkin 200 comprises a liquid pervious topsheet 222, a liquid impervious backsheet 223, an absorbent core 224, side flaps 234, an adhesive fastening means 236 and removable release liners 237.

Sanitary napkin 200 can also be provided with one or more additional layers or components. These include an acquisition layer (or the "secondary topsheet") 201 positioned generally between the topsheet 222 and the absorbent core 224. The sanitary napkin 200 may also include a nonwoven layer 202 positioned between the absorbent core 224 and the backsheet 223. The nonwoven layer 202 serves to keep the material of the core 224 from tearing (when the core is comprised of cross-linked cellulose fibers) and the layers of the sanitary napkin 200 are stitched together.

Secondary topsheet 201, absorbent core 224, and nonwoven 202 are all intermediate the topsheet 222 and the backsheet 223. Depending upon the desired characteristics for the sanitary napkin 200, one or more of these intermediate layers may be provided in a sanitary napkin. In addition, there are other materials and components which may serve useful as an intermediate layer between the topsheet 222 and the backsheet 223 to provide the desired characteristics, e.g., fluid movement, storage capacity, fluid acquisition, fluid distribution, resilience, flexibility, thickness, or any combination of the above. It will be obvious to one skilled in the art that the intermediate layer, the layer between the topsheet 222 and the absorbent core 223, may be any layer or layers which serves to provide specific functions for the sanitary napkin 200.

Figure 7:
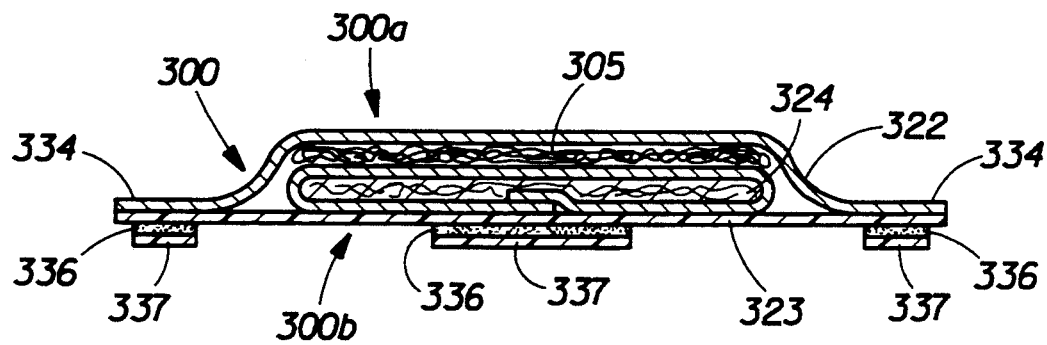
FIG. 7 is a cross-sectional view of another embodiment of a sanitary napkin of the present invention.

Referring now to FIG. 7 another embodiment of a sanitary napkin 300 is illustrated. The sanitary napkin 300 has a body surface 300a and a garment surface 300b. The sanitary napkin 300 comprises a liquid pervious topsheet 322, a liquid impervious backsheet 323, an absorbent core 324, side flaps 334, adhesive fastening means 336 and removable release lines 337. The sanitary napkin 300 also includes a layer of capillary channel fibers 305. Capillary channel fibers 305 are fibers having channel formed therein, preferably, on their exterior surfaces. FIGS. 8 to 12C shows examples of some types of capillary channel fibers 305 which may be used as an intermediate layer in sanitary napkin 300. Suitable capillary channel fibers are described below, and in the following patent applications which were filed on Jul. 23, 1991: U.S. patent application Ser. No. 07/734,404 filed in the names of Thompson et al.; U.S. patent application Ser. No. 07/734,392 filed in the names of Thompson et al.; and U.S. patent application Ser. No. 07/734,405 filed in the names Buenger et al. These patent applications may be referred to collectively the "Capillary Channel Fiber" patent application. Suitable capillary channel fibers are also described in EPO Patent Application 0 391 814 published Oct. 10, 1990.

While a variety of capillary channel fibers can be used herein, the following description discusses some preferred characteristics of the capillary channel fibers 305 that are incorporated into the sanitary napkin 300 intermediate the topsheet 322 and the backsheet 323.

The capillary channel fibers 305 used herein can be prepared from any convenient polymer which is substantially nonswelling when wet. Polymers such as polyethylene, polypropylene, polyesters (preferred), and the like, are useful herein, so long as they are spinnable such that they can be formed with external capillary channels, as noted hereinabove. Conveniently, the polymers are melt-extrudable. Typically, the capillary channel fibers herein will be prepared from a synthetic polyethylene terephthalate polymer melt having an inherent viscosity ("IV") of from about 0.6 to about 0.9. (IV is a term of art and can be determined in well-known fashion. See, for example, U.S. Pat. No. 4,829,761 at column 8.) The IV of a polymer melt bears some relationship to the ability of the polymer to retain the shape of the capillary channel walls, and is related to the average molecular weight of the polymers. For example, it is convenient to employ a polyester having an inherent viscosity of about 0.7 herein, but it would be more preferred to employ a polymer having an inherent viscosity of about 0.9.

The capillary channel fibers 305 preferably have a denier in the range of about 10 to about 22. However, it is to be understood that the denier of the fibers used is within the discretion of the formulator, and the denier per fiber can easily be in the range of about 5 to about 35.

The depth:width ratio of the capillary channels herein is preferably in the range of about 0.5 to about 2.5. Typical and readily producible capillary channel fibers which are quite satisfactory for use herein thus have a depth-of-walls of about 46 microns and a width-between-walls of about 33 microns. The walls, themselves, are typically about 3–15 microns thick. Although variations in these dimensions are acceptable, capillary channel fibers prepared from polyester and having these characteristics are quite effective for their intended purpose. Such fibers can be prepared using conventional equipment and readily withstand pressures of the type encountered in sanitary devices, especially sanitary napkins and pantiliners, without collapse or spreading of the capillary channel walls to such an extent that their capillary function is lost.

The capillary channels 329 can be of various shapes. Certain shapes can offer particular advantages in particular product applications. For example, "U"-shaped, "H"-shaped, "C"-shaped with stabilizing legs depending therefrom and "V"-shaped capillary channels 305 may be used. Furthermore, the basic shapes may be repeated (see Figures), or even branched, to produce fibers containing multiple channels, but it will be appreciated that when more than about three repeating shapes are used, some additional stiffness may be noted in the fibers. The multiple "U" fibers of FIG. 11 offer the additional advantages of having additional capillarity due to face-to-face contact and being easily curled.

The manufacture of capillary channel fibers 305 of the type employed herein is described in EPO Application 391,814 and in co-pending U.S. Continuation-In-Part Application entitled "Fibers Capable of Spontaneously Transporting Fluids", Serial No. 07/736,261, filed Jul. 23, 1991, Inventors Phillips, Jones et al., Eastman Chemical Company; co-pending U.S. Patent Application entitled "Spinneret Orifices and Filament Cross-Sections with Stabilizing Legs Therefrom", Ser. No. 07/918,174, filed Jul. 23, 1992, Inventors Phillips, et al.; and in co-pending U.S. Patent Application entitled "Open Capillary Channel Structures, Improved Process for Making Capillary Channel Structures, and Extrusion Die for Use Therein", Ser. No. 07/482,446, filed Feb. 20, 1990, inventors Thompson and Krautter.

While the polymers used to prepare the capillary channel fibers herein are not, themselves, water-absorbent (nor are they absorbent to urine or blood-containing fluid such as menses), the fibers themselves are most preferably hydrophilic. Since most synthetic polymers are hydrophobic, the capillary channel fibers herein are surface-treated in order to render them hydrophilic.

The surface treatment of polymeric fibers involves processes which are well-known in the extensive fiber literature. In general, such processes involve treating the surface of the fibers with a "hydrophilizing agent", especially a surfactant. {Hydrophilization, which results in wettability of the fibers by aqueous fluids, can routinely be measured, for example, using contact angle measurements. In general, a contact angle less than 90° indicates a hydrophilic surface. A CAHN Surface Force Analyzer (SFA 222) can be used to measure hydrophilicity, as can a variety of other instruments known in the art.) Typical surfactant useful in such processes include various nonionic and anionic detersive surfactants of the general type known in the laundry literature. Hydrophilizing agents include wetting agents such as polyethylene glycol monolaurates (e.g., PEGOSPERSE 200 ML, a polyethylene glycol 200 monolaurate available from Lonza, Inc., Williamsport, Pa., USA), and ethoxylated oleyl alcohols (e.g., VOL-PO-3, available from Croda, Inc., New York, N.Y., USA). Other types of hydrophilizing agents and techniques can also be used, including those well known to those skilled in the fiber and textile arts for increasing wicking performance, improving soil release properties, etc. Hydrophilizing agents can be added to the polymer at various stages prior to use, though preferably prior to drawing of the capillary channel fibers to their final size. For example, the hydrophilizing agent can be added in advance to the polymer prior to melting or blended into the polymer subsequent to melting. The additive hydrophilizing agent can also be applied to the polymer subsequent to formation, e.g., subsequent to exit from an extrusion die in a melt, wet, or dry spinning process, preferably prior to drawing of the fiber to small diameter. Of course, since the articles herein are intended to come into contact with sensitive regions of the human body, it is preferred that surfactants used to hydrophilize the surfaces of the capillary channel fibers be nontoxic and nonirritating to human skin. Various surfactant treatments for hydrophilizing the capillary channel fibers are described in the Examples hereinafter. Another method for hydrophilizing fibrous surfaces involves subjecting said surfaces to ionizing radiation, e.g., in a plasma, and such methods have the advantage that there is no surfactant residue on the surface of the fibers. Whatever the means, the overall objective is to secure capillary channel fibers for use herein which are spontaneously wettable by the fluids they are intended to transport.

Figure 13:
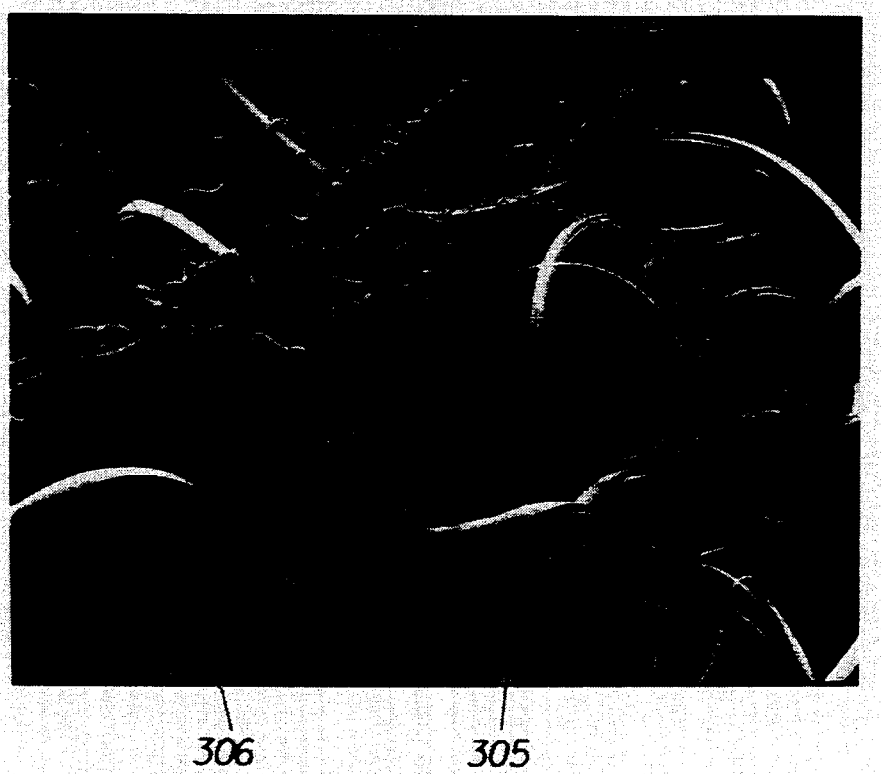
FIG. 13 is a photomicrograph (21.4×) of a structure which may be utilized as an intermediate layer in the sanitary napkin of the present invention.

A preferred structure for the intermediate layer is shown in FIG. 13. The intermediate layer is comprised of curled or helically crimped capillary channel fibers 305 and bicomponent binder fibers 306. The bicomponent binder fibers 306 preferably have a round cross-section with an outer sheathing layer of lower melt temperature than that of the inner core. The outer sheathing layer should be a material which bonds with the lower melt temperature layer of the topsheet 322. Methods for forming the intermediate layer include carding, rando process, needlepunch, hydroentangled, and the like.

3. Method of Making

Figure 4:
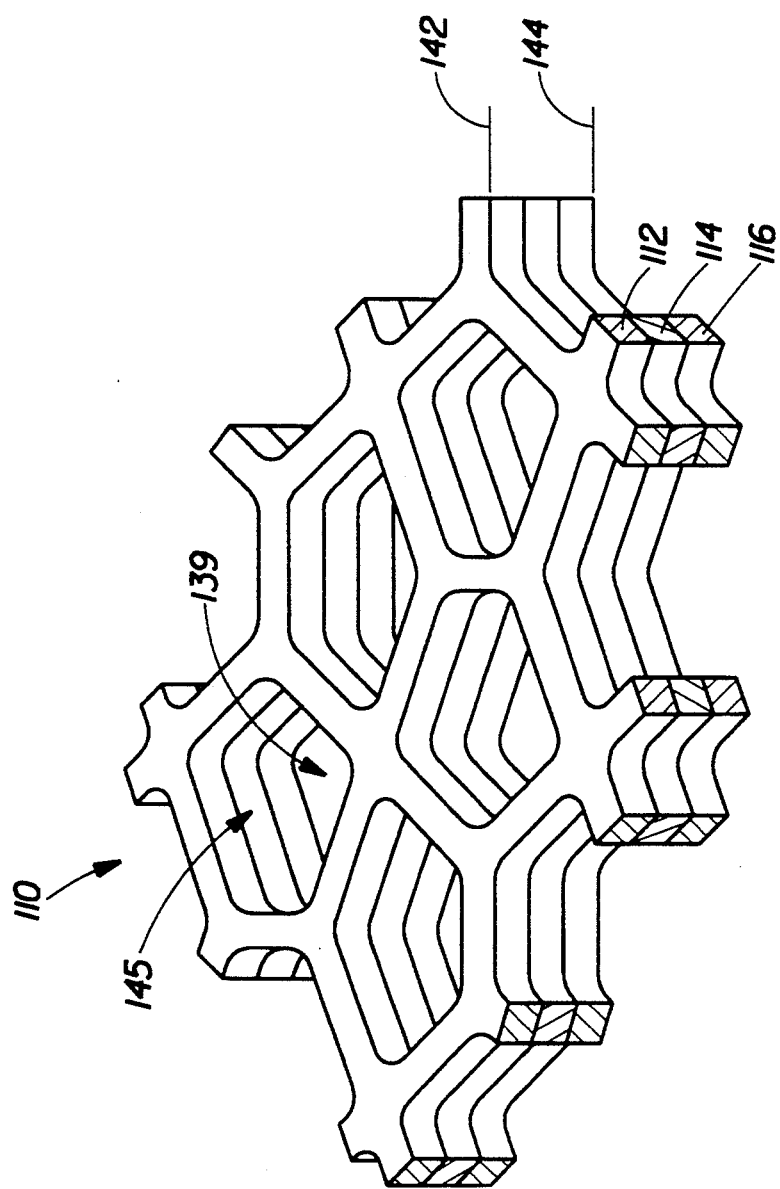
FIG. 4 is an enlarged, partially segmented, perspective illustration of a photoetched laminate structure of the type used to form the web illustrated in FIG. 3.

FIG. 4 is an enlarged, partially segmented perspective illustration of a photoetched laminate structure 110 utilized to form an initially impervious, substantially planar, heated, coextruded plastic film to produce a fluid pervious web 10 of the type generally illustrated in FIG. 3. The laminate structure 110 is comprised of a stack of individual lamina 112, 114 and 116. Each lamina has a pattern of openings therein. Lamina 112, 114 and 116 have the identical pattern. In practice it is typical to employ several lamina having the identical pattern superposed upon one another to provide sufficient depth of pattern to the plastic web 10.

A comparison of FIG. 4 with the fiber-like plastic web 10 shown in FIG. 3 reveals the correspondence of capillary opening 45 in the uppermost plane 42 of plastic web 10 to opening 145 in the uppermost plane 142 of the photoetched laminate structure. Likewise, capillary opening 39 in the lowermost plane 44 of plastic web 10 corresponds to the lowermost opening 139 in the lowermost plane 144 of the photoetched laminate structure 110.

Processes for constructing laminate structures of the type generally disclosed in FIG. 4 are disclosed in U.S. Pat. No. 4,342,314 issued to Radel et al. on Aug. 3, 1982, said patent being hereby incorporated herein by reference. The photoetched laminate structures are then preferably rolled by conventional techniques into a tubular forming member. Methods for constructing tubular forming members are disclosed in U.S. Pat. No. 4,342,314 issued to Radel et al. on Aug. 3, 1982; U.S. Pat. No. 4,508,256 issued to Radel et al. on Apr. 2, 1985; and U.S. Pat. No. 4,509,908 issued to Mullane, Jr. on Apr. 9, 1985, said patents being incorporated herein by reference.

A preferred method for forming a coextruded three-dimensional plastic structure of the present invention is to apply a molten web onto a tubular forming structure directly from a coextruder. The molten film is drawn by a vacuum to cause the molten web to conform to the tubular forming structure thereby forming a three-dimensional, macroscopically expanded plastic structure of the present invention. Such a method of forming a three-dimensional plastic structure is well known to those skilled in the art.

Another preferred method for converting a ribbon of thermoplastic film into a three-dimensional structure of the type herein disclosed is by applying a high pressure fluid jet comprised of water or the like against one surface of the film, preferably while applying a vacuum adjacent the opposite surface of the film. Such methods are generally described in greater detail in commonly assigned U.S. Pat. No. 4,609,518 issued to Curro et al. on Sep. 2, 1986; U.S. Pat. No. 4,629,643 issued to Curro et al. on Dec. 16, 1986; U.S. Pat. No. 4,637,819 issued to Ouellette et al. on Jan. 20, 1987; U.S. Pat. No. 4,681,793 issued to Linman et al. on Jul. 21, 1987; U.S. Pat. No. 4,695,422 issued to Curro et al. on Sep. 22, 1987; U.S. Pat. No. 4,778,644 issued to Curro et al. on Oct. 18, 1988; U.S. Pat. No. 4,839,216 issued to Curro et al. on Jun. 13, 1989; and U.S. Pat. No. 4,846,821 issued to Lyons et al. on Jul. 11, 1989, each of said patents being hereby incorporated herein by reference.

Figure 5:
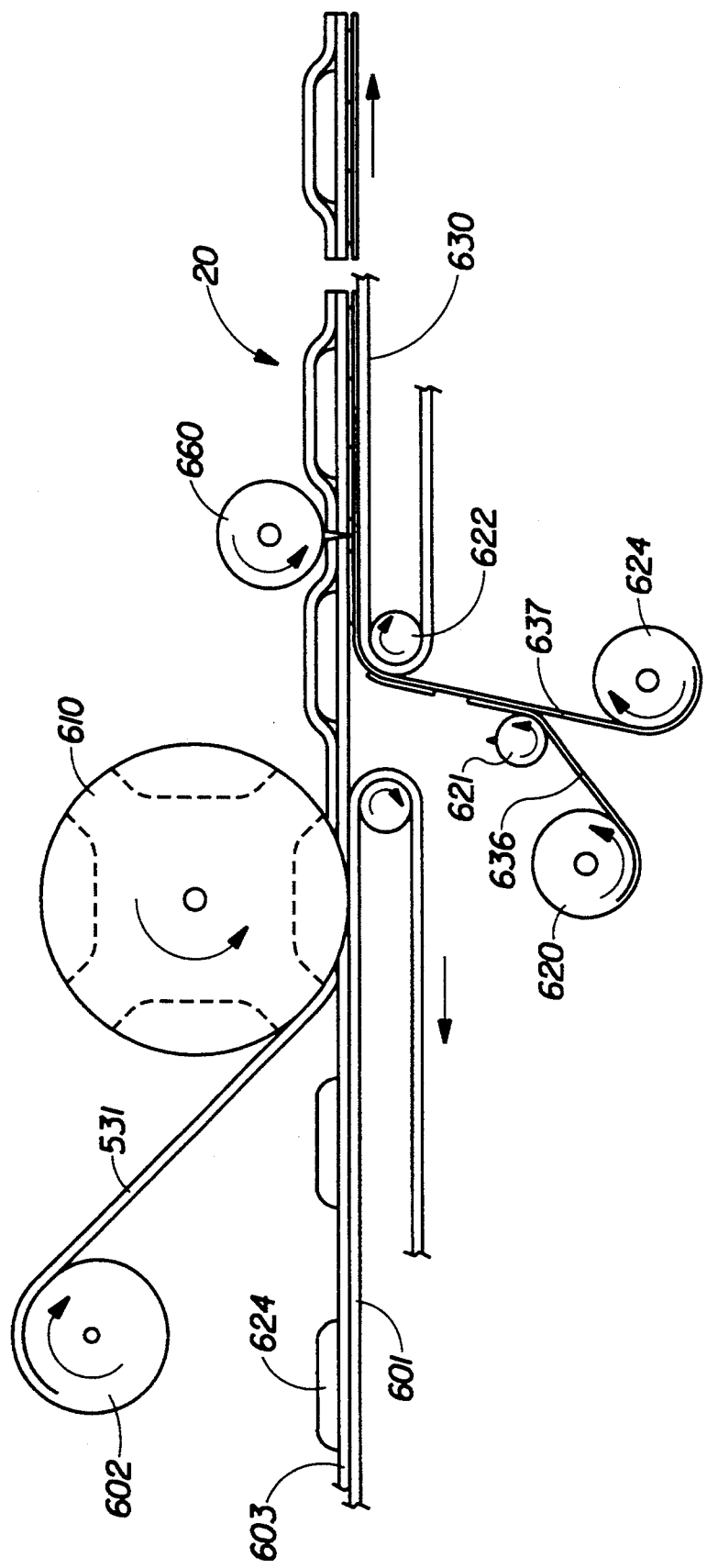
FIG. 5 is a schematic illustration of the assembly of sanitary napkins.

FIG. 5 is a schematic illustration of the assembly of sanitary napkins 20 of the present invention. Preferably, a continuous ribbon of backsheet material 603 is fed along conveyor 601 toward heat roll 610. Absorbent cores 624 preferably have been formed and secured to continuous ribbon of backsheet material 603 by processes well known in the art prior to reaching heat roll 610, Together absorbent core 624 and backsheet ribbon 603 are fed toward heat roll 610 along conveyor 601. Concurrently a continuous ribbon of coextruded topsheet material 531 is fed from roll 602 toward assembly station 610. As topsheet ribbon 531 enters assembly station 610 it is heated to a temperature in excess of that of the lower melting point temperature but less than that of the higher melting point temperature. Accordingly the layer of polymeric material having the lower melting point temperature is thereby thermally bonded to the absorbent core 624 and the backsheet 603. The thermal bonding of the web of topsheet material 531 occurs along the sidewalls of the fiber-like elements, The greatest amount of thermal bonding occurs between the tips of the sidewall portions of the fiber-like elements of the the polymeric material having the lower melting point temperature and the absorbent core and the backsheet. The portions of the fiber-like elements corresponding with the base portion and the sidewall portion remote from the second surface of the polymeric web may also bond with the absorbent core or the backsheet, The resilient characteristics of the fiber-like material are maintained and the web maintains its compliant and flexible characteristics. This is compared to a two-dimensional film which would be bonded along its entire surface thus creating a relatively stiff and ridged material which is both undesirable and uncomfortable for the wearer. In addition to maintaining its resiliency and flexibility, the web of topsheet material 531 also provides the additional standoff to separate the wearer from the moisture which is then absorbed within the absorbent core 624, thus providing the user with a drier and more comfortable sanitary napkin.

In another preferred embodiment, the absorbent core and backsheet may be heated to a temperature between the first melting point temperature and the second melting point temperature. Thus as the web of topsheet material contacts the heated core and backsheet the polymeric material with the lower melting point temperature thermally bonds to the backsheet and the absorbent core.

As the continuous ribbon of absorbent articles leaves assembly station 610 it is fed toward knife 660. Prior to reaching knife 660 a continuous ribbon of securement material 636 is fed from continuous roll 620 toward roller 622. Prior to reaching roller 622 continuous ribbon of securement material 636 is cut into discrete segments at knife 621 where it is secured to release liner 637. Release liner 637 is fed from continuous roll 624 toward roller 622. At roller 622 the discrete segments of securement material 636 and release liner 637 are secured to backsheet 603. Knife 660 then cuts continuous ribbon of absorbent articles into discrete absorbent articles 20. Conveyer 630 then feds absorbent articles 20 toward a packaging and assembly station as are well known in the art.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. An absorbent article including a fluid pervious topsheet, a fluid impervious backsheet joined to said topsheet, and an intermediate layer positioned between said topsheet and said backsheet, said topsheet comprising: a resilient, three-dimensional, macroscopically expanded, apertured, fluid pervious web including a first polymeric film material which exhibits a first melting point temperature and a second polymeric film material bonded to said first polymeric material to form a laminate, said laminate having a thickness, said second polymeric material exhibits a melting point temperature which is less than said first melting point temperature, said web having first and second surfaces spaced apart by a distance greater than the thickness of said laminate, said web having a plurality of capillaries extending from said first surface to said second surface, said capillaries being defined by a plurality of sidewall portions interconnected to one another intermediate said first and said second surfaces and terminating in said second surface, such that when said web is heated to a temperature between said first melting point temperature and said second melting point temperature said second polymeric material of said sidewall thermally bonds to said intermediate layer.

2. The absorbent article according to claim 1, wherein said intermediate layer is an absorbent core.

3. The absorbent article according to claim 1, wherein said intermediate layer is a secondary topsheet.

4. The absorbent article according to claim 1, wherein said intermediate layer comprises capillary channel fibers.

5. The absorbent article according to claim 1, wherein said first polymeric material comprises polyetheylene and said second polymeric material comprises ethylene vinyl acetate.

6. The absorbent article according to claim 1, wherein said absorbent article is a sanitary napkin.

7. The absorbent article according to claim 1, wherein said absorbent article is a disposable diaper.

8. The absorbent article according to claim 1, wherein said intermediate layer comprises capillary channel fibers and bicomponent binder fibers.

9. The absorbent article according to claim 8, wherein said capillary channel fibers are curled.

10. The absorbent article according to claim 1, wherein said laminate comprises an uppermost layer and a lowermost layer.

11. The absorbent article according to claim 10, wherein said uppermost layer is comprised of said first polymeric material.

12. The absorbent article according to claim 10, wherein said uppermost layer is comprised of said second polymeric material.

13. An absorbent article including a fluid pervious topsheet, a fluid impervious backsheet joined to said topsheet, and an intermediate layer positioned between said topsheet and said backsheet, said topsheet comprising: a resilient, three-dimensional, macroscopically expanded, apertured, fluid pervious web including a first polymeric film material forming an uppermost layer which exhibits a first melting point temperature and a second polymeric film material forming a lowermost layer bonded to said first polymeric material to form a laminate, said laminate having a thickness, said second polymeric material exhibits a melting point temperature which is less than said first melting point temperature, said web having first and second surfaces spaced apart by a distance greater than the thickness of said laminate, said web having a plurality of capillaries extending from said first surface to said second surface, said capillaries being defined by a plurality of sidewall portions interconnected to one another intermediate said first and said second surfaces and terminating in said second surface, such that when said web is heated to a temperature between said first melting point temperature and said second melting point temperature said lowermost layer thermally bonds to said intermediate layer.

14. The absorbent article according to claim 13, wherein said intermediate layer is an absorbent core.

15. The absorbent article according to claim 13, wherein said intermediate layer is a secondary topsheet.

16. The absorbent article according to claim 13, wherein said intermediate layer comprises capillary channel fibers.

17. The absorbent article according to claim 13, wherein said intermediate layer comprises capillary channel fibers and bicomponent binder fibers.

18. An absorbent article including a fluid pervious topsheet, a fluid impervious backsheet joined to said topsheet, and an intermediate layer positioned between said topsheet and said backsheet, said topsheet comprising: a resilient, three-dimensional, macroscopically expanded, apertured, fluid pervious web including a first polymeric film material forming a lowermost layer which exhibits a first melting point temperature and a second polymeric film material forming an uppermost layer bonded to said first polymeric material to form a laminate, said laminate having a thickness, said second polymeric material exhibits a melting point temperature which is less than said first melting point temperature, said web having first and second surfaces spaced apart by a distance greater than the thickness of said laminate, said web having a plurality of capillaries extending from said first surface to said second surface, said capillaries being defined by a plurality of sidewall portions interconnected to one another intermediate said first and said second surfaces and terminating in said second surface, such that when said web is heated to a temperature between said first melting point temperature and said second melting point temperature said uppermost layer thermally bonds to said intermediate layer.

19. The absorbent article according to claim 18, wherein said intermediate layer is an absorbent core.

20. The absorbent article according to claim 18, wherein said intermediate layer is a secondary topsheet.

21. The absorbent article according to claim 18, wherein said intermediate layer comprises capillary channel fibers.

22. The absorbent article according to claim 18, wherein said intermediate layer comprises capillary channel fibers and bicomponent binder fibers.

* * * * *